US006354242B1

(12) United States Patent
Pardue et al.

(10) Patent No.: US 6,354,242 B1
(45) Date of Patent: Mar. 12, 2002

(54) METHODS FOR GAMETE PRODUCTION IN BIRDS

(75) Inventors: Samuel L. Pardue; James N. Petitte; Susan D'Costa, all of Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/533,141

(22) Filed: Mar. 23, 2000

(51) Int. Cl.⁷ .......................... A01K 45/00; A61K 35/54
(52) U.S. Cl. ......................................... 119/6.8; 424/582
(58) Field of Search ............................ 119/6.8; 424/582

(56) References Cited

U.S. PATENT DOCUMENTS

| | | | | |
|---|---|---|---|---|
| 5,438,954 A | * | 8/1995 | Phelps et al. | 119/6.8 |
| 5,784,992 A | | 7/1998 | Petitte et al. | 119/6.8 |
| 5,817,320 A | * | 10/1998 | Stone | 424/278.1 |
| 5,830,510 A | | 11/1998 | Petitte et al. | 424/582 |

FOREIGN PATENT DOCUMENTS

| WO | WO 93/14629 | 8/1993 | A01K/67/04 |
|---|---|---|---|
| WO | WO 93/15185 | 8/1993 | C12N/5/00 |

OTHER PUBLICATIONS

Chang et al.: Production Of Germline Chimeric Chickens By Transfer Of Cultured Primordial Germ Cells, *Cell Biology International* 21:8, 495–499 (1997).
Kagami et al.: Sexual Differentiation Of Chimeric Chickens Containing ZZ And ZW Cells In The Germline, *Molecular Reproductive Development*. 42, 379–387 (1995).
Kagami et al.; The Developmental Origin Of Primordial Germ Cells And The Transmission Of The Donor–Derived Gametes In Mixed–Sex Germline Chimeras To The Offspring In The Chicken, *Molecular. Reproductive Development* 48, 501–510 (1997).
Kino et al.; Production Of Chicken Chimeras From Injection Of Frozen–Thawed Blastodermal Cells, *Poultry Science*, 76, 753–760 (1997).
Mueller et al.; Chimeric Pigs Following Blastocyst Injection Of Transgenic Porcine Primordial Germ Cells, *Mol. Reprod. Dev.* 54, 244–254 (1999).
Naito et al.; Production Of Germline Chimeric Chickens, With High Transmission Rate Of Donor–Derived Gametes, Produced By Transfer Of Primordial Germ Cells, *Mol. Reprod. Dev.* 39, 153–161 (1994).
Naito et al.; Preservation Of Chick Primordial Germ Cells In Liquid Nitrogen And Subsequent Production Of Viable Offspring, *Journal of Reproduction and Fertility* 102, 321–325 (1994).
Naito et al.; Donor Primordial Germ Cell–Derived Offspring From Recipient Germline Chimaeric Chickens: Absence Of Long Term Immune Rejection And Effects On Sex Ratios, *British Poultry Science* 39, 20–23 (1998).

Naito et al.; Differentiation Of Donor Primordial Germ Cells Into Functional Gametes In The Gonads Of Mixed–Sex Germline Chimeric Chickens Produced By Transfer Of Primordial Germ Cells Isolated From Embryonic Blood, *Journal of Reproduction and Fertility* 117:2, 291–298 (1999).
Ono et al.; Transfer Of Male Or Female Primordial Germ Cells Of Quail Into Chick Embryonic Gonads, *Exp. Anim.* 45, 347–352 (1996).
Reynaud; Transfert de cellules germinales primordiales de dindon a l'embryon de poulet par injection intravasculaire, *J. Embryol. Exp. Morphol* 21, 485–507 (1969).
Reynaud; Capacites reproductrices et descendence de Poulet ayant submi un transfert de cellules germinales primordiales durant la vie embryonnaire, *Arch. Dev. Bio.* 179, 85–110 (1976).
Shaw et al.; The Fate Of Female Donor Blastodermal Cells In Male Chimeric Chickens, *Biochem. Cell. Biol.* 70, 1218–1229 (1992).
Simkiss et al.; Female Chromosomes In Cockerel Ejaculates, *Proc. R. Soc. Lond. B. Biol. Sci.* 263, 1245–1249 (1996).
Tagami et al.; Differentiation Of Female Chicken Primordial Germ Cells Into Spermatozoa In Male Gonads, *Dev. Growth. Differ.* 39, 267–271 (1997).
Tagami et al.; Developmental Origin Of Avian Primordial Germ Cells And Its Unique Differentiation In The Gonads Of Mixed–Sex Chimeras, *Mol. Reprod. Dev.* 50:3, 370–376 (1998).
Tajima et al.; Production Of Germline Chimera By Transfer Of Primordial Germ Cells In The Domestic Chicken, *Theriogenology* 40, 509–519 (1993).
Tajima et al., Production Of Germ–Line Chimeras By Transfer Of Cryopreserved Gonadal Primordial Germ Cells (gPGCs) In Chicken, *J. Expt. Zool.* 280, 265–267 (1998).
Thoraval et al.; Somatic And Germline Chicken Chimeras Obtained From Brown And White Leghorns By Transfer Of Early Blastodermal Cells, *Poultry Science* 73, 1897–1905 (1994).
Yasuda et al.; A Method To Obtain Avian Germ–Line Chimaeras Using Isolated Primordial Germ Cells, *J. Reprod. Fertil.* 96, 521–528 (1992).

* cited by examiner

*Primary Examiner*—Charles T. Jordan
*Assistant Examiner*—Yvonne R. Abbott
(74) *Attorney, Agent, or Firm*—Myers Bigel Sibley & Sajovec

(57) ABSTRACT

A method for the production and collection of avian sperm comprises the steps of: providing primordial germ cells from a donor avian species; administering the primordial germ cells to a recipient avian species in ovo; incubating the recipient avian species to hatch; and then collecting sperm of the donor avian species from the recipient avian species. For example, the donor avian species may be a whooping crane, and the recipient avian species may be a sand hill crane. In another example, the donor avian species may be a turkey, and the recipient avian species may be a chicken.

22 Claims, No Drawings

METHODS FOR GAMETE PRODUCTION IN BIRDS

FIELD OF THE INVENTION

The present invention concerns methods of transferring primordial germ cells to birds for the production of gametes therein. Such methods are useful in the conservation of endangered avian species, in reducing the time required to produce spermatozoa from slowly maturing species such as turkeys, decreasing the costs of maintaining breeder flocks, and altering the sex ratio of offspring flocks (e.g., to enhance the efficiency of production).

BACKGROUND OF THE INVENTION

The ability to more easily produce gametes of particular avian species would be extremely useful to the avian veterinary and poultry production fields. For endangered species such as the whooping crane, it would be extremely useful to have a ready supply of male spermatozoa. For commercial birds such as turkeys, it would be desirable to more quickly and economically produce male spermatozoa. For meat- producing flocks, it is desirable to have ways to increase the ratio of male birds in the flock. Accordingly, there is a need for new ways to obtain avian spermatozoa.

Chimeras are composite organisms consisting of cells derived from more than one zygote. Experimental chimeras have been used to study cell to cell interaction and cell lineage analysis during development (A. McLaren, *Mammalian Chimeras*. Cambridge University Press, Cambridge (1976)). When chimeras are produced using material derived from very early embryos, organisms develop containing a full mixture of somatic tissues. If the starting material includes early germ cells or their precursors, the resulting individuals will produce gametes of both the donor and recipient genotypes. In addition, chimeras can be intraspecific, i.e. between two zygotes of the same species, or interspecific, i.e. between two different species.

Avian primordial germ cells (PGCs) like other vertebrate germ cells are extragonadal in origin and must undergo a complex journey to reach the gonad. The transfer of blastodermal cells and primordial germ cells has produced avian germline chimeras.

Reynaud (*J. Embryol. Exp. Morphol.* 21:485–507 (1969)), a pioneer in the production of avian germline chimeras, reported the production of turkey-chicken germline chimeras by the intravascular transfer of dissociated turkey germinal crescent cells into previously sterilized chick embryos (accomplished by exposure of the recipient germinal crescent to ultra-violet light). PGCs obtained by mechanical dissociation of the endoderm of the germinal crescent (stage 5) were injected into the blood vessels of chicken embryos (3–5 days of incubation). Prior to injection the recipient embryos were sterilized at stage 8–10 (H&H) with ultraviolet light; however, the sterilization was not complete. The turkey PGCs in the chick embryo were identified solely on the basis of their nucleoplasmic ratio. This method of identification was difficult and tenuous and could not be used for actively dividing turkey PGCs since the dividing germ cells gave an aberrant nucleoplasmic ratio. In a succeeding study, the transferred PGCs were allowed to undergo maturation in the host gonads and apparently could give rise to gametes but they were not suitable for fertilization (Wilhelm Roux *Arch. Dev. Bio.* 179:85–110 (1976)). The spermatozoa were incapable of fertilizing turkey eggs. They fertilized chick eggs but there was no normal development. Chicken spermatozoa were capable of activating the eggs obtained from female interspecific chimeras but they did not give rise to embryos. When the eggs were fertilized by turkey spermatozoa they developed into abnormal embryos that did not survive beyond stage 38 (H&H). Reynaud used morphology as the only distinguishing characteristic in an attempt to identify turkey germ cells from chicken germ cells. Morphology alone is not sufficient for identifying chimeras and must be substantiated with other markers. In addition, according to Aige-Gil and Simkiss (*Brit. Poul. Sci.* 32:427–438 (1991)), the presence of turkey gametes was not identified by test matings. Accordingly, there remains a need for new ways to accomplish the production and transfer of avian gametes.

SUMMARY OF THE INVENTION

A method for the production and collection of avian sperm comprises the steps of: providing primordial germ cells from a donor avian species; administering the primordial germ cells to a recipient avian species in ovo; incubating the recipient avian species to hatch; and then collecting sperm of the donor avian species from the recipient avian species. For example, the donor avian species may be a whooping crane, and the recipient avian species may be a sand hill crane. In another example, the donor avian species may be a turkey, and the recipient avian species may be a chicken.

In birds, unlike mammals, it is the male that is the homogametic sex (ZZ) and the female which is the heterogametic sex (Zw). Therefore in birds, it is the female that determines the gender of the offspring since she produces ova which carry either the Z or w chromosome. Thus, as noted below, by transferring male primordial germ cells to female embryonic hosts, the percentage of Z-bearing ova produced by that host is increased and the percentage of male offspring is increased. An increase in the percentage of male offspring from broiler flocks is economically desirable for the corresponding greater feed conversion ratio and more efficient meat production so obtained.

Accordingly, a second aspect of the present invention is a method of increasing the number of male birds hatched from a plurality of bird eggs, comprising the steps of: administering to a female bird in ovo male (ZZ) avian primordial germ cells; incubating the female bird to hatch; raising the female bird to sexual maturity; and then breeding the bird to produce a plurality of fertile bird eggs (with the ratio of male to female birds eggs produced from the bird being greater than that obtained in the absence of administering the male primordial germ cells to the bird in ovo.) Typically, the method further comprises the step of incubating the plurality of bird eggs to hatch (with the ratio of male to female birds produced from the plurality of eggs being greater than that produced in the absence of administering the male primordial germ cells to the female bird in ovo). The female bird may be of any suitable species, such as chicken or turkey, and the primordial germ cells being administered are preferably from the same species as the female bird to which they are administered.

The foregoing and other objects and aspects of the present invention are explained in detail in the specification set forth below.

DETAILED DESCRIPTION OF THE PREFERRED EMBODIMENTS

"Bird" or "avian species" as used herein refers to any avian species, including but not limited to chicken, turkey, duck, geese, quail, pheasant, and ostrich. Any of numerous other species can be employed to carry out the present invention, particularly when it is used for the conservation of endangered species such as the whooping crane (where the recipient species would be the sand hill crane). "Egg" as used herein refers to avian eggs that contain live embryonic birds. "Primordial germ cell" or "PGC" as used herein refers to the most differentiated diploid cell line in the embryo that will ultimately develop into haploid gametes (either sperm or ova).

"SSEA-1 antibody" refers to an antibody, preferably a monoclonal antibody, that specifically binds to the stage specific embryonic antigen-1 (SSEA-1) (M. Buehr *Exp. Cell Res.* 232, 194–207 (1997)). SSEA-1 is a carbohydrate epitope determined by galactose β1→4 fucose α1→3 N acetylglucosamine linkage (H. Gooi et al., *Nature* 292, 156–158 (1981)). A monoclonal antibody to SSEA-1 was developed by the fusion of mouse myeloma cells with spleen cells from a mouse that had been immunized with F9 teratocarcinoma cells (D. Solter and B. Knowles, *Proc. Natl. Acad. Sci. USA* 75, 5565–5569 (1978)). SSEA-1 antibody is known as an avian immunohistochemical germ cell marker (L. Karagenc et al., *Dev. Genet.* 19, 290–301 (1996)). Particularly preferred is clone MC 480, which may be obtained from the Developmental Studies Hybridoma Bank, The University of Iowa, Iowa City, Iowa, USA.

Primordial germ cells may be provided and formulated for carrying out the present invention by any suitable technique, and stored, frozen, cultured or the like prior to use as desired. For example, the primordial germ cells may be collected from donor embryos at an appropriate embryonic stage (see, e.g., (V. Hamburger and H.L. Hamilton, *A Series of Normal Stages in the Development of the Chick, Journal of Morphology*, 88, 49–92 (1951) (These stages referred to as H&H stages herein) stage 4, or the germinal crescent stage, through stage 30, with cells being collected from blood or gonad in the later stages). The primordial germ cells are, in general, twice the size of somatic cells and easily distinguished and separated therefrom on the basis of size. Male (or homogametic) primordial germ cells (ZZ) can be distinguished from heterogametic primordial germ cells (Zw) by any suitable technique, such as collecting germ cells from a particular donor and typing other cells from that donor, the collected cells being of the same chromosome type as the typed cells. Cell may be formulated for administration to animals by dissociating the cells (e.g., by mechanical dissociation) and intimately admixing the cells with a pharmaceutically acceptable carrier (e.g., phosphate buffered saline solution). The primordial germ cells are preferably gonadal primordial germ cells or blood primordial germ cells ("gonad" or "blood" referring to their tissue of origin in the original embryonic donor), and are most preferably gonadal primordial germ cells. The primordial germ cells administered may be heterogametic (Zw) or homogametic (ZZ) depending upon the particular object of the administration. PGCs are preferably administered in physiologically acceptable carrier, preferably at a pH of from about 6 to about 8 or 8.5, in a suitable amount to achieve the desired effect (e.g., 100 to 1000 PGCs per embryo). The PGCs may be administered free of other ingredients or cells, or other cells and ingredients may be administered along with the PGCs.

Administration of the primordial germ cells to the recipient animal in ovo may be carried out at any suitable time at which the PGCs can still migrate to the developing gonads. In general, it is preferred that administration be carried out from stage 13 or 14 through stage 18 (H&H) of embryonic development, and most preferably stage 15. For chickens, the time of administration is thus during days 1, 2, 3 or 4 of embryonic development, most preferably day 2 to day 2.5. Administration is typically by injection into any suitable target site, such as the region defined by the amnion (including the embryo), the yolk sac, etc. Injection into the embryo itself (including the embryo body wall) is preferred, and intravascular or intracoelomic injection into the embryo are particularly preferred. The methods of the present invention may be carried out with or without prior sterilization of the recipient bird in ovo. (by "sterilization" is meant render substantially incapable of producing gametes). In a preferred embodiment of the invention, the primordial germ cells are conveniently administered to a recipient subject in ovo that has not been previously sterilized. When donor gametes are collected from such a recipient, they may be collected as a mixture with gametes of the donor, and may be used as such a mixture or the mixture processed to enrich the proportion of donor gametes therein.

Administration of PGCs may be carried out by administering PGCs per se, or by administering precursors cells that develop into PGCs in the subject (particularly where the invention is employed to alter the sex ratio of offspring). For example, administration may be carried out by injecting the bird with blastodermal cells, where the blastodermal cells differentiate into primordial germ cells in vivo in the bird.

When used for the production and collection of avian gametes (sperm, ova), the primordial germ cells are administered in ovo to a recipient species that is different from the donor species from which the PGCs were obtained. The recipient is then incubated to hatch and raised to sexual maturity, and sperm cells or ova of the donor species collected from the recipient animal, all in accordance with standard techniques. For example, in the case of an endangered species, the donor avian species may be a whooping crane, and the recipient avian species may be a sand hill crane. In another example concerning commercial poultry production, the donor avian species may be a turkey, and the recipient avian species may be a chicken.

When used for increasing the number or ratio of male birds hatched from a group of eggs, the present invention involves administering to a female bird in ovo male avian primordial germ cells. The gender of the bird in ovo may be predetermined or determined after hatch. The bird is then incubated to hatch, the gender of the bird determined if necessary, raised to sexual maturity, and bred by crossing the bird with a suitable male breeder stock in accordance with known techniques. A plurality of fertile eggs laid by that bird are then collected, and typically incubated to hatch and the resulting birds grown for at least two to three weeks. The ratio of male to female bird eggs (or birds) produced from the female bird is greater than that obtained in the absence of administering the male primordial germ cells to that bird in ovo. Such methods are typically used on species of bird that are raised for meat production, such as chickens, turkeys, ducks, etc.

The in ovo administration of the primordial germ cells may be carried out by any suitable technique, either manually or in an automated manner. Injection is preferred. The mechanism of in ovo administration is not critical, but it is preferred that the method not unduly damage the tissues and organs of the embryo or the extraembryonic membranes surrounding it so that the treatment will not unduly decrease hatch rate. A hypodermic syringe fitted with a needle of about 18 to 26 gauge is suitable for the purpose. Depending on the precise stage of development and position of the embryo, a one-inch needle will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria. It is envisioned that a high speed injection system for avian embryos will be particularly suitable for practicing the present invention. Numerous such devices are available, exemplary being the EMBREX INOVOJECT™ system (described in U.S. Pat. Nos. 4,681,063 and 4,903,625 to Hebrank), and U.S. Pat. Nos. 4,040,388; 4,469,047, and 4,593,646 to Miller. The disclosure of all United States patent references cited herein are be incorporated herein by reference in their entirety. All such devices, as adapted for practicing the present invention, comprise an injector containing the a formulation of the primordial germ cells as described herein, with the injector positioned to inject an egg carried by the apparatus in the appropriate location within the egg as discussed above. In addition, a sealing apparatus operatively with the injection apparatus may be provided for sealing the hole in the egg after injection thereof.

The present invention is described in greater detail in the following non-limiting Examples.

EXAMPLES 1–8

Material and Methods

Example 1

Plasmid Isolation and Verification

Transformed DH5 alpha cells provided by Dr. M. Matzke were streaked onto LB plates containing the antibiotics ampicillin (20 µg/ml)+methicillin (80 µg/ml) and grown overnight at 37° C. Six individual colonies were picked and grown overnight in 10 ml LB containing the above antibiotics. Plasmid DNA was isolated from the 6 different colonies using the Qiagen mini prep protocol. To verify the identity of the plasmid the undigested plasmids, linearized plasmid (EcoR I) and the double-digest (EcoR I+Hind III) were separated on a 2% agarose gel. Two of the six colonies containing the insert were subsequently used for large scale plasmid isolation (Qiagen). The undigested parent plasmid (puc18), undigested recombinant plasmids, linearized plasmid (EcoR I/ Hind III/ BamH I) and double-digested plasmid (EcoR I+Hind III and EcoR I+BamH I) were separated on 2% gel to confirm the identity of the plasmid isolated.

Example 2

PCR labeling of TM1 Probe

A pair of primers was synthesized based on their ability to amplify the insert in the multicloning site of the parent puc1 8 plasmid. They were M13 puc reverse=5' AAC AGC TAT GAC CAT G and M13 puc forward=5' GTA AAA CGA CGG CCA GT. The optimized PCR mixture consisted of 3 mM $MgCl_2$ in Taq buffer (Idaho Tech) 0.5 µM each primer, 50 ng of DNA (TM1) circular denatured plasmid, 5 units of Taq polymerase (Promega), 10 µl of PCR dig-labeling mix (Boehringer Mannheim). The reaction volume was made up to 100 µl with sterile water, PCR conditions consisted of an initial denaturation at 96° C. for 5 min followed by 30 cycles consisting of denaturation (94° C.) for 45 seconds, annealing (50° C.) for 55 seconds followed by extension at 72° C. for 60 seconds. The PCR was performed in "The Mini Cycler" Model PTC 150 (MJ Research Inc., Massachusetts). After amplification the entire sample was electrophoresed on a 2% gel. The labeled insert was eluted from the gel using the Qia quick gel extraction kit (Qiagen) according to manufacturer recommendations. The probe was stored at −20° C. and used for dot blot and in situ hybridization. Prior to storage the yield of the DIG-labeled DNA was estimated according to the Genius system user's guide for filter hybridization (Boehringer Mannheim).

Example 3

Dot Blot Hybridization

To verify the accuracy, sensitivity and specificity of the TM1 insert, serial dilution of male and female turkey DNA (0–500 ng), chicken male and female DNA (0–2 µg) and parent plasmid containing the TM1 insert (10 ng–1 pg) were denatured and spotted onto nitrocellulose paper. The blot was baked at 80° C. for an hour and then used for hybridization. Prehybridization and hybridization were carried out using the Engler-Blum procedure (*Anal Biochem.* 210:235–244 (1993)). Hybridization was carried out overnight at 68° C.; probe concentration used was 2.5 ng cDNA probe/ml.

After hybridization and stringency washes the blot was placed in washing buffer (0.1M Maleic Acid, 0.15 M NaCl pH 7.5). The membrane was incubated in blocking solution (wash buffer+3% Tween 20) for 30 minutes and then placed in blocking solution containing anti-digoxigenin alkaline phosphatase conjugate for half an hour. The membrane was subsequently washed in washing buffer twice and then incubated in detection buffer (0.1 M Tris HCl, 0.1 m NaCl, 50 mM $MgCl_2$ pH 9.5). Hybrids were finally detected using the chemiluminescent substrate CDP-STAR™ (from Boehringer-Mannheim, Germany). Blots were exposed to X-ray film for at least 5 minutes.

Example 4

Production of Interspecific Turkey-Chicken Embryonic Germline Chimeras

Fertilized turkey eggs were incubated at 38.5° C. for 8–8.5 days (stage 27–28 H&H). Embryos were dissected to obtain gonads. The gonads were collected in DMEM and 10% FBS and dispersed by passing them through a 30-gauge needle. The cells were cultured in DMEM and 10% FBS until confluence (3–5d). The stromal cells dispersed and formed a confluent layer while the germ cells were loosely attached to the stromal cells. The germ cells were collected by gentle pipetting and counted. Approximately 150–300 cells in 3–5 µl of medium were injected into the sinus terminalis of 60 or 72-hour chick embryos. The embryos were then incubated in 100 mm petri dishes or in their own eggshells at 38.5° C. for 2–5 days. After incubation, DNA was isolated from the embryos (n=18) and used for dot blot analysis with the dig-labeled probe TM 1.

Example 5

In Situ Hybridization

The in situ hybridization was performed on paraffin sections and cryosections. This procedure is based on the protocol by Rolighed and Lindeberg (see J. Rolighed, Detection of HPV II DNA in paraffin—embedded laryngeal tissue with a DIG-labeled DNA probe. In *Non-radioactive In Situ Hybridization Application Manual Beohringer Mannheim Second Edition*, pp 122–125 (1996)) with some modifications.

Paraffin Sectioning: Gonads were isolated from turkey embryos (day 9) and chick embryos at corresponding stages, fixed overnight in 4% paraformaldehyde at 4° C. The gonads were washed in PBS three times for a total of 90 minutes. They were the dehydrated, embedded in paraffin and sectioned (10 microns). Sections were collected on Probe—On Plus™ slides (Fisher Scientific). The sections were baked at 60° C. for 30 minutes, dewaxed in xylene and rehydrated through graded ethanol series (99%—water). The sections were treated with Proteinase K (50 μg/ml and 100 μg/ml) in TES (50 mM Tris HCl pH 7.4, 10 mM EDTA and 10 mM NaCl) for 12 to 25 minutes at 37° C. and at room temperature.

Cryosectioning: The trunk region of day 8.5 turkey embryos was fixed overnight at 4° C. in 4% paraformaldehyde in PBS. Varying concentrations of proteinase K in TES from 0 to 45 μg/ml for 10, 15 or 20 minutes at 37° C. were tested. The 0.67 μg/ml and 1.25 μg/ml at 37° C. for 15 min was the optimal proteolytic treatment for the embryonic tissues.

Preparation of probe/blind cocktail: The probe cocktail consisted of 10 μl of 50×Dendharts solution, 50 μl of dextran sulphate (50%), 10 μl of salmon sperm DNA (9.4 mg/ml), 100 μl of 20×SSC, 500 ng of digoxigenin labeled TM1 probe and distilled water was added for a final volume of 250 μl. Finally 250 μl of formamide was added to the cocktail. The blind cocktail contained all the above components except the labeled TM1 probe. The cocktail was mixed by vortexing and stored at −20° C.

Hybridization: After proteolytic digestion both the paraffin and cryosections were fixed in 0.4% paraformaldehyde for 5 minutes at 4° C. The sections were then washed in distilled water (5 minutes) and air-dried. Then 10 or 15 μl of probe cocktail or blind cocktail (negative control) was added over each section. Siliconized cover slips were placed on the sections prior to denaturation at 95° C. for 6 minutes. The slides were then placed for a minute on ice and placed in a humid chamber for 16–20 hours at 42° C. The stringency washes and detection of the hybrid was similar to that described by Rolighed and Lindeberg (see above), except the ready-made alkaline phosphatase substrate NBT/BCIP (Amresco) was used for detection of hybrids. After detection, slides were counter stained with aqueous eosin for a few seconds and washed. Samples were mounted in an aqueous mounting medium made from 10 grams of gelatin dissolved in 60 ml of water at 70° C.–80° C. to which 70 ml of glycerin and 1 ml of phenol was added.

Example 6

Production of Interspecific Chicken-Turkey Embryonic Chimeras

Barred Rock chicken embryos were incubated until stage 23–25 (H&H). The genital ridges along with some of the adjoining tissue from ten embryos was collected in DMEM, supplemented with 10% FBS, glutamine, antibiotic and antimycotic solution. They were then rinsed twice in PBS and incubated in 0.02% EDTA at 37° C. for fifteen minutes. Fresh media was added and the ridges were teased using needles. The entire cell suspension was collected in a 15 ml tube and the clumps were allowed to settle for a couple of minutes. The cell suspension was collected and spun at 1500 rpm for 5 minutes. The media was replaced and cell viability determined using trypan blue exclusion. Aliquots of the cell suspension were taken and stained with SSEA-1 antibody to determine the number of germ cells injected. Approximately 5 μl of cell suspension containing 25–30 PGCs (percentage of PGCs in cell suspension was approximately 3.2%) were injected into the blood vessel of each Nicholas turkey embryo (n=10) at stages 13–14 (H&H) of development. The embryos were incubated in glass dishes covered with plastic wrap at 37.5° C. until stages 21–25. The entire trunk region of the recipient embryos was fixed in 4% paraformaldehyde overnight at 4° C., washed thrice in PBS for a total time of 90 min, embedded in gelatin/sucrose, frozen and sectioned.

As turkey gonadal PGCs are SSEA-1 negative and chicken gonadal PGCs are SSEA-1 positive, the antibody against SSEA-1 can be used to identify the transfer donor chick PGCs in the embryonic germline chimeras.

Example 7

Production of Interspecific Turkey-Chicken Embryonic Germline Chimeras

Fertilized turkey eggs were incubated at 38.5° C. for 8–8.5 days (stage 27–28 H&H). Embryos were dissected to obtain gonads. They were collected in PBS and incubated in 0.02% EDTA at 37° C. for twelve minutes. Fresh media was added and the ridges were teased gently using needles. The entire cell suspension was collected and spun at 1500 rpm for 5 minutes. The media was replaced and cell viability determined. The entire cell suspension was preplated at 37° C. in DMEM +10% FBS for 6–7 hours. After culture the non-adherent cells were gently collected and centrifuged. Then 2–3 μl of cell suspension containing approximately 150 PGCs was injected into the blood vessels stage 14 (H&H) chick embryos. The recipient eggs were sealed and incubated at 37.5° C. Recipient embryos were collected at different stages of incubation from stage 19 until stage 25. The embryos were rinsed in PBS thrice and then fixed in 4% paraformaldehyde overnight at 4° C. They were washed thrice in PBS; the total time varied depending on the thickness of the embryo. The embryos were placed in 50% ethanol and embedded in paraffin. The sections were dewaxed, rehydrated and rinsed in PBS.

The controls for the double staining technique (see below) were transverse sections of two stage 26 chick embryos and two stage 24-turkey embryos. Forty-two sections of the chick genital region and all serial sections of the turkey genital region were stained.

A total of eight recipient chick embryos were serially sectioned. Five of the eight embryos were fixed at stages 19 & 20. Two embryos were fixed at stage 22 & 23. The last embryo was fixed at stage 25. A majority of the stage 19 & 20 sections were used for double staining. Only the alternate sections of stage 22, 23 and 25 embryos were used for the double staining.

Example 8

Double Staining with SSEA-1 Antibody and PAS Stain

Immunohistochemical studies were carried out using the Vectastain ABC- AP kit (Vector Laboratories, Burlingame, California). Sections were rinsed thrice in PBS for a total time of 30 minutes. They were then blocked in 1.5% goat serum in PBS for 20 minutes to eliminate nonspecific binding. Subsequently, sections were incubated for an hour in primary monoclonal antibody against SSEA-1 (clone MC 480 obtained from the Developmental Studies Hybridoma Bank, The University of Iowa, Iowa City, Iowa). After a rinse in PBS, embryonic sections were incubated in biotinylated secondary antibody (30 min) then rinsed in PBS and incubated in Vectastain ABC-AP reagent (30 min). After a final wash in PBS they were stained in the alkaline phosphatase substrate NBT/BCIP (Amresco, Solon, Ohio) for 20 min.

Following immunohistochemical staining the sections were rinsed in tap water and placed in periodic acid for 6 min. The sections were then rinsed in water for 10 min and stained in Schiff reagent for 15 min. After rinsing them in tap water the sections were mounted in the aqueous mounting medium.

EXAMPLES 9–15

Results

Matzke et al. (*Chromosoma* 102:9–14 (1992)) have characterized a repetitive DNA sequence that is enriched on the turkey microchromosomes. It is a 41 bp repeat element represented on 5% of the genome (approximately $2.2 \times 10^6$ copies in diploid genome of a cell). Hence, this species-specific DNA sequence was used in DNA—DNA hybridization to test if it could be used to identify turkey DNA in chick embryos.

Example 9

Plasmid Isolation and Verification

Based on gel electrophoresis analysis, the parent plasmid: puc 18 was 2.69 kb while the linearized recombinant plasmid obtained from Dr. Matzke was approximately 2.8 kb long. Double-digestion of the plasmid DNA from colonies number 2 and 5 released an insert of approximately 0.15–0.17 kb. This verified that the transformed DH5 cells sent to us contained the appropriate recombinant plasmid. The plasmid contained the TM1 fragment (149 bp) consisting of three copies of the turkey-specific 41 bp repeat.

Example 10

PCR Labeling of TM1 Probe

PCR amplification of circular plasmid DNA along with digoxigenin—labeled nucleotides resulted in the production of an amplification product of approximately 0.19–0.20 kb. The increase in size of the amplification product compared to the insert (0.15–0.17 kb) is probably due to incorporation of multiple DIG-labeled nucleotides. The PCR labeled probe was subsequently used in both the dot blot hybridization experiments and DNA—DNA in situ hybridization.

Example 11

Dot Blot Hybridization

The results of the Dot Blot Hybridization (data not shown) indicated the probe bound to both male and female turkey DNA samples with equal intensity. Thus verifying that the probe is not sex-specific. Hybridization was done on serial dilutions of turkey DNA from 500 ng to 0 ng of turkey DNA. The probe detected as low as 0.30 ng of turkey DNA. Hybridization with 0 to 2 micrograms of male as well as female chicken DNA confirmed that the probe was species-specific and it did not bind to chicken DNA. Varying concentrations of turkey DNA (10 ng–0 ng) was mixed with 0–2 µg of chicken DNA. Hybridization with this mixture of DNA indicated that as little as 1.25 ng of turkey DNA could be detected in 1 µg of chicken DNA.

Example 12

Production of Interspecific Turkey-Chicken Embryonic Germline Chimeras

No interspecific turkey-chicken embryonic germline chimeras could be detected using the above dot blot hybridization protocol. The inability to detect chimeras could be due to an intrinsic biological barrier that would prevent migration of turkey gonadal PGCs to the chicken gonad. It could also be due to a technical problem, i.e. the procedure (dot blot hybridization) was not sensitive enough to identify the few donor germ cells in the chicken gonad. The latter reason seemed more likely; hence, an attempt was made to develop a more sensitive technique i.e. in situ hybridization to localize the donor PGCs in the recipient.

Example 13

In Situ Hybridization Analysis of Turkey Sections

Theoretically, the in situ marker system would be an appropriate marker for identifying donor (turkey) cells in a chimera. As the marker is within the nuclei, it is ubiquitous and does not leak out to other cells or affect development of the recipient embryo. In the present study, the TM1 sequence selectively bound to DNA in turkey nuclei (data not shown). No positive signal was detected in chicken cells (data not shown) or sections incubated with blind cocktail (data not shown), indicating that the probe was species-specific and without non-specific signal. Ideally in the positive control sections of turkey embryos every nucleus should have stained positive. However, only a small percentage of cells stained positive (data not shown). In addition, there was variation in the signal intensity between different cell populations in the same section under identical digestion conditions. This indicated that there were false negatives associated with this technique. A decrease in the percentage of false negatives might be accomplished by lowering the stringency conditions. However, this could also lead to false positives. In embryonic germline chimeras the donor cells would represent a very small percentage of the total embryonic section or cells. In addition, this marker system identifies only a minority of positive turkey cells. Hence, in situ hybridization with the TM 1 probe would not be an efficient way of identifying chimeras.

Example 14

Identification of Interspecific Chicken-Turkey Embryonic Chimeras using SSEA-1 Staining In order to confirm that we did not have technical problems associated with the procedure, interspecific chicken-turkey germline chimeras were produce by the intravascular transfer of chicken gonadal germ cells. As there is a species difference in the expression of the SSEA-1 antigen on chick and turkey gonadal PGCs, it was hypothesized that SSEA-1 antibody could be used to identify chicken-turkey embryonic germline chimeras. Of the five embryos that survived four were cryosectioned. In one of the four embryos, nineteen SSEA-1 positive cells were identified in the dorsal mesentery of the turkey embryos (data not shown), an additional four SSEA-1 labeled chick germ cells were identified in the turkey genital ridge (data not shown). In the second, embryo two SSEA-1 positive cells were identified in the vicinity of the gonad. In the remaining two embryos no donor PGCs were identified.

Based on these results gonadal PGCs from day 5 chick embryos (stage at which PGCs are SSEA-1 positive) when injected intravascularly into a stage 13 turkey embryo are capable of remigration, colonizing the gonad and giving rise to germline chimeras. Thus, it appears that the chemoattractant produced by the turkey gonad is not species-specific. It also reconfirmed that chicken gonadal PGCs retain their ability to migrate even after they have colonized the gonad. The lower efficiency of germline chimeras in this study could be due to the lower number of donor PGCs in the injected cell suspension.

Example 15

Identification of Interspecific Turkey-Chicken Embryonic Chimeras using SSEA-1 and PAS Staining Previous research has identified a species difference in the expression of SSEA-1 by turkey and chick PGCs. This antigenic variation coupled with the standard PAS test could potentially be used for identifying turkey-chick germline chimeras. Observations of the double stained chick embryonic sections verified that chick PGCs are both PAS positive and SSEA-1 positive (data not shown). No PAS positive, SSEA-1 negative germ cells were observed in the chick control sections. Double staining of the stage 24 turkey sections with PAS and SSEA-1 verified that turkey PGCs migrating through the dorsal mesentery and colonizing the gonad are PAS positive and do not express the SSEA-1 epitope (data not shown). Hence, double staining of chick and turkey embryos verified that the double staining technique could be used as a marker for identifying turkey germ cells in a chick gonad. Using the SSEA-1 antibody along with the standard PAS stain, germline chimeras were detected in four out of eight recipient chick embryos (Table 1). Approximately 24 hours after injection of turkey PGCs into the blood vessels of chick embryos SSEA-1 negative and PAS positive turkey germ cells were identified in the chick embryos. Turkey PGCs were identified along with the chick PGCs in the thickened coelomic epithelium (data not shown). The epithelium was located in between the coelomic angle and the mesonephros, the site of the future gonad. In the older embryos (stage 22 and 23) donor turkey PGCs were observed in both recipient chick embryos. Some germ cells were located in the dorsal mesentery (data not shown), others had migrated further and had colonized the chick gonad (data not shown). Analysis of potential chimeras with the double staining technique verified that turkey gonadal PGCs can be used to produce interspecific chimeras.

TABLE 1

Production of turkey—chicken embryonic germline chimeras

| Stage | No. of Embryos Sectioned | No. of Germline Chimeras |
|---|---|---|
| 19/20 | 5 | 2/5 |
| 22/23 | 2 | 2/2 |
| 25 | 1 | 0/1 |

Although the DNA-DNA hybridization was species-specific, the procedure was unable to detect chimeras. The dot blot hybridization procedure was not sensitive enough to identify the donor PGCs whereas the in situ hybridization procedure had a high percentage of false negatives associated with it. The double staining procedure appears to be a successful way of identifying turkey-chicken chimeras. Based on the above results gonadal PGCs from chick and turkey embryos when injected intravascularly are capable of remigration to the gonad and giving rise to germline chimeras. Thus, it appears that the chemoattractant produced by the avian gonad is not species-specific. It also confirms that gonadal PGCs retain their ability to migrate even after they have colonized the gonad.

The production of turkey-chicken chimeras has wide applications. The transfer of male turkey PGCs is useful for turkey spermatogenesis in chicken gonads. This could accelerate spermatogenesis because the time required for production of sperms in chickens is 18 weeks as compared to 30 to 32 weeks in turkeys. The ability to culture PGCs and make germline chimeras could reduce the number of superior turkey sires currently needed to produce offspring. The ability to produce turkey sperm from a smaller and cheaper bird might also benefit the poultry industry.

The experimental chimeras could also provide a model to study the interaction between germ cells and somatic cells of different genotypes whereby it becomes possible to inquire whether its neighboring cells impose any of the germ cell characteristics upon it. This technique could also be utilized to transfer PGCs from low fecundity strains to more prolific birds, and for preserving PGCs in case of unexpected death or disease or in case an avian species is endangered under natural mating conditions (A. Tajima et al., *Theriogenology* 40:509–519 (1993)).

The foregoing is illustrative of the present invention, and is not to be construed as limiting thereof. The invention is defined by the following claims, with equivalents of the claims to be included therein.

That which is claimed is:

1. A method for the production and collection of avian gametes, comprising the steps of:

providing primordial germ cells from a donor avian species;

administering said primordial germ cells to a recipient avian species in ovo, wherein said recipient avian species is a different species from said donor avian species;

incubating said recipient avian species to hatch;

raising said recipient avian species to sexual maturity; and then collecting gametes of said donor avian species from said recipient avian species.

2. A method according to claim 1, wherein said donor avian species is a whooping crane.

3. A method according to claim 2, wherein said recipient avian species is a sand hill crane.

4. A method according to claim 1, wherein said donor avian species is a turkey.

5. A method according to claim 4, wherein said recipient avian species is a chicken.

6. A method according to according to claim 1, wherein said administering step is carried out by in ovo injection.

7. A method according to claim 1, wherein said primordial germ cells are selected from the group consisting of gonadal primordial germ cells and blood primordial germ cells.

8. A method according to claim 1, wherein said administering step is carried out at stage 13 to stage 18 of recipient embryonic development.

9. A method according to claim 1, wherein said primordial germ cells carry a pair of male determinative (Z) chromosomes.

10. A method according to claim 1, wherein said primordial germ cells carry a female determinative (w) chromosome.

11. A method according to claim 1, wherein said administering step is carried out without prior sterilization of said bird in ovo.

12. A method of increasing the number of male birds hatched from a plurality of bird eggs, comprising:

administering to a female bird in ovo male (ZZ) avian primordial germ cells;

incubating said female bird to hatch;

raising said female bird to sexual maturity; and then breeding said bird to produce a plurality of fertile bird eggs;

with the ratio of male to female birds eggs produced from said bird being greater than that obtained in the absence of administering said male primordial germ cells to said bird in ovo.

13. A method according to claim 12, wherein said primordial germ cells are the same species as said female bird.

14. A method according to claim 12, wherein said female bird is a chicken.

15. A method according to claim 12, wherein said female bird is a turkey.

16. A method according to according to claim 12, wherein said administering step is carried out by in ovo injection.

17. A method according to claim 12, wherein said primordial germ cells are selected from the group consisting of gonadal primordial germ cells and blood primordial germ cells.

18. A method according to claim 12, wherein said administering step is carried out at stage 13 to stage 18 of recipient embryonic development.

19. A method according to claim 12, wherein said administering step is carried out without prior sterilization of said female bird in ovo.

20. A method according to claim 12, further comprising the step of incubating said plurality of bird eggs to hatch;

with the ratio of male to female birds produced from said plurality of eggs being greater than that produced in the absence of administering said male primordial germ cells to said female bird in ovo.

21. A method according to claim 12, wherein said administering step is carried out by injecting said bird with primordial germ cells.

22. A method according to claim 12, wherein said administering step is carried out by injecting said bird with blastodermal cells, and wherein said blastodermal cells differentiate into primordial germ cells in said bird.

* * * * *